United States Patent [19]

Skurkovich et al.

[11] Patent Number: 4,581,010

[45] Date of Patent: * Apr. 8, 1986

[54] METHOD OF IMMONOSUPPRESSION AFTER TRANSPLANTATION OF CELLS, TISSUES AND ORGANS

[76] Inventors: Simon V. Skurkovich; 261 Congressional La., #709, Rockville, Md. 20852

[*] Notice: The portion of the term of this patent subsequent to Dec. 7, 1999 has been disclaimed.

[21] Appl. No.: 446,713

[22] Filed: Dec. 3, 1982

Related U.S. Application Data

[63] Continuation-in-part of Ser. No. 247,205, Mar. 24, 1981, Pat. No. 4,362,155.

[51] Int. Cl.$^4$ .............................................. A61M 1/03
[52] U.S. Cl. ......................................... 604/4; 604/5; 260/112 B
[58] Field of Search ................ 128/214 R; 260/112 B; 424/85, 93, 94; 604/4–6

[56] References Cited

U.S. PATENT DOCUMENTS 4,168,261  9/1979  Edy .
4,172,071  10/1979  De Maeyer et al. .
4,362,155  12/1982  Skurkovich .................... 128/214 R

FOREIGN PATENT DOCUMENTS 1562546  6/1976  United Kingdom .

OTHER PUBLICATIONS

William Ganong, Review of Medical Physiology, p. 383 (1975).
Nature, 247:551 (Feb. 22, 1974).
Nature, "Immunosuppressive Effect of an Anti-Interferon Serum", vol. 35, Dec. 1975; S. V. Skurkovich et al.
Immunology, "Stimulation of Transplantation Immunity and Plasma Cell Reaction by Interferon in Mice"; vol. 25, 1973, pp. 317–322; S. V. Skurkovich et al.

Primary Examiner—C. Fred Rosenbaum
Assistant Examiner—Mario Costantino
Attorney, Agent, or Firm—Gilbert Wells

[57] ABSTRACT

Immunosuppression after transplantation of cells, tissues, and organs is achieved by clearing interferon, or interferon in combination with other substances from the bloodstream of a patient being treated.

4 Claims, 2 Drawing Figures

4,581,010

METHOD OF IMMONOSUPPRESSION AFTER TRANSPLANTATION OF CELLS, TISSUES AND ORGANS

This is a continuation-in-part of U.S. Ser. No. 247,205 filed Mar. 24, 1981, now U.S. Pat. No. 4,362,155 granted Dec. 7, 1982.

FIELD OF THE INVENTION

The present invention relates to immunosuppression for the treatment of patients after transplantation of cells, tissues and organs, and more particularly it relates to immunosuppression by clearing interferon or interferon in combination with other substances from the bloodstream of a patient being treated.

BACKGROUND ART

In that application, included herein in its entirety by reference, autoimmune diseases and allergy connected with the hyperproduction of interferon in a patient's body are treated by the removal of interferon from the bloodstream.

An article published in *Nature*, 247:551, Feb. 22, 1974 reports demonstration in mice that administration of anti-interferon serum induces an immunosuppressive effect. Another article related to transplantation was published in *Immunology*, Vol. 25, 1973, pages 317 to 322. It reported the demonstration that small doses of interferon accelerate mouse skin allograft rejection, in addition to an increase in the cytotoxic action of lymphocytes on target cells in vitro.

At present time immunosuppressive therapy in transplant patients includes the administration to the body of strong chemical, biological and hormonal agents, which have a wide range of side effects.

An object of this invention is to provide methods of achieving immunosuppression after transplantation of cells, tissues and organs by the extracorporeal removal of biologically active substances participating in the mechanism of rejection from the body of patients.

Other objectives, features and advantages of the invention will be found throughout the following description, drawings and claims.

DISCLOSURE OF THE INVENTION

In order to achieve immunosuppression after the transplantation of cells, tissues, and organs such as heart, kidney, bone marrow, skin, etc., this invention provides for the selective clearing from the blood of a patient an agent which participates in the development of immune response, namely interferon.

Clearing interferon from the blood as defined herein includes absorption, disintegration, deactivation or suppression of the biological activity of the interferon. This is achieved extracorporeally or otherwise by administration of an anti-interferon agent in the bloodstream of the patient.

BRIEF DESCRIPTION OF THE DRAWINGS

In the detailed description of the preferred embodiments of the invention hereinafter presented, reference is made to the accompanying drawings, in which.

THE PREFERRED EMBODIMENTS

The present description will be directed in particular to elements forming part of, or cooperating more directly with, the present invention. Elements not specifically shown or described herein are understood to be selectable from those known in the art.

Figure 1:
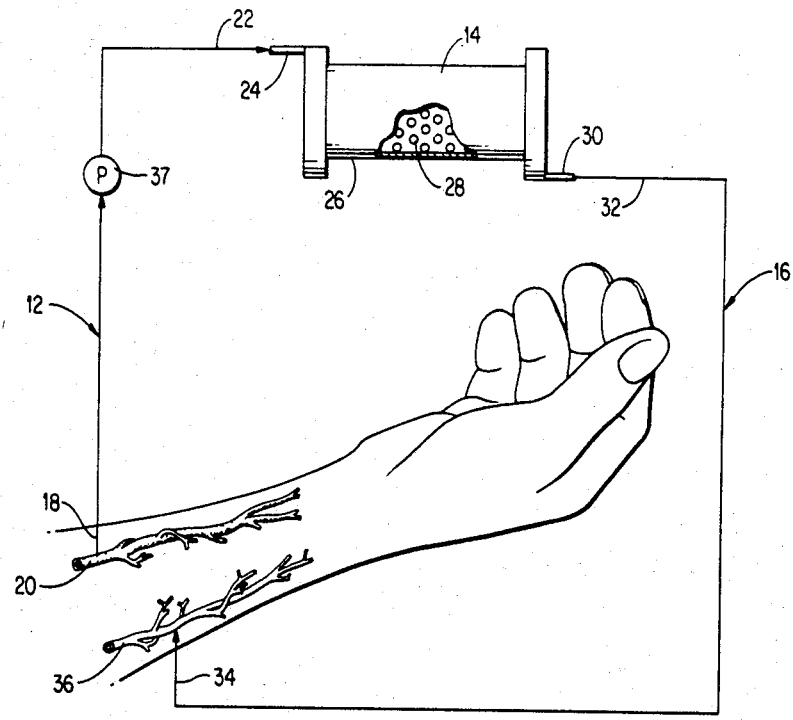
FIG. 1 is a schematic illustration of one embodiment apparatus provided by the present invention.

Referring now to the drawings, and to FIG. 1 in particular, one embodiment of an apparatus for treatment of blood to clear from interferon is illustrated. The apparatus, which is generally designated 10, comprises an inlet tube 12, means 14 for clearing the blood from interferon, and an outlet tube 16. The inlet tube 12 has an inlet end 18 connected to a cannula (not shown) inserted into blood vessel 20 of a patient. The outlet end 22 of the inlet tube 12 is connected to the inlet 24 of a housing 26 containing a plurality of porous glass beads 28, such as those described in U.S. Pat. No. 4,168,261. The outlet 30 of the housing 26 is connected to an end 32 of the outlet tube 16. The other (outlet) end 34 of tube 16 is connected to a cannula (not shown) inserted into a vein 36 of the patient. Preferably, a pump 37 is included in the apparatus 10. The inlet tube 12 provides means for removing whole blood from a patient, and the outlet tube 16 provides means for returning the blood to the patient. As clearly illustrated in FIG. 1, the tubes 12 and 16 and the means 14 are in continuous fluid communication with each other.

In operation, the cannula connected to the inlet 18 is inserted into blood vessel of the patient, and the cannula connected to the outlet 34 is inserted into a vein. When a pump is used, the pump is then actuated to pump blood from the patient through the housing 24 so that the beads 28 can remove interferon from the blood. Preferably, all of the interferon is removed from the blood. Blood free from interferon is then returned through the outlet tube 16 into the vein of the patient.

The method used with this embodiment of the invention provides a continuous process for the achievement of post transplantation immunosuppression. The process involves removing blood from a patient, passing the removed blood through means for clearance of interferon from the blood and returning the blood, which is free from interferon, to the patient.

Figure 2:
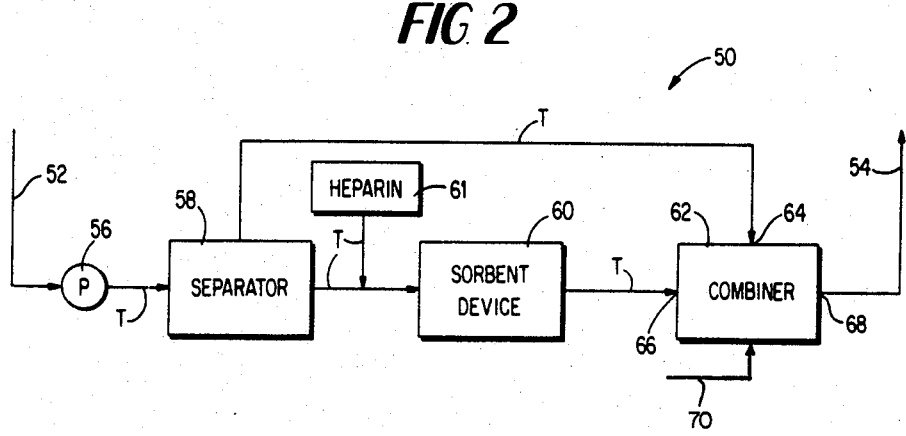
FIG. 2 is a schematic block diagram of another embodiment of the present invention.

Referring now to FIG. 2, another embodiment of an apparatus according to the present invention, generally designated 50, is illustrated. The apparatus 50 includes an inlet tube, generally designated 52, and an outlet tube, generally designated 54. The inlet tube 52 is similar to the inlet tube 12, and the outlet tube 54 is similar to the outlet tube 16 of the embodiment illustrated in FIG. 1. A pump 56 is provided to pump blood from a patient into a separator 58. A suitable separator is a plasma filter of the type described in British Pat. No. 1,562,546. Other suitable methods of plasmapheresis, such as centrifugation, also are usable to separate plasma or plasma with leukocytes from the whole blood. The plasma, or plasma with leukocytes, if fed from the separator 58 to a sorbent containing device 60 charged with the aforementioned anti-interferon antibodies. Such device can be the means 14 for removing interferon described in connection with FIG. 1, in general, a device using a process of the type described in U.S. Pat. No. 4,172,071, or any other suitable method using a capacious sorbent for interferon carried by a solid support. The plasma, or plasma with leukocytes, after passing through sorbent within the device 60, rejoins the formed elements of blood removed from the whole blood by the separator 58. A combiner 62 is illustrated for providing the mixing function. Such combiner need be no more complex than a mixing valve having one inlet 64 connected to the separator 58 and a second inlet 66 connected to the device 60. The outlet 68 of the valve is connected to the outlet tube 54. A device 61 for adding heparin to the plasma, or plasma with leukocytes, is positionable between the separator 58 and the device 60. Sections of tubing T interconnect the pump 56, the separator 58, the device 60, the device 61, and the combiner 64, as illustrated in FIG. 2. Thus, the various components of the apparatus 50 are in fluid communication with each other.

The method of treating blood for the development of immunosuppression utilizing the apparatus of FIG. 2 involves the connecting of the inlet and outlet tubes to blood vessel and a vein, respectively, of a patient to be treated; pumping the whole blood of the patient to a separator; separating plasma, or plasma with leukocytes, from blood cells within the separator; passing the plasma, or plasma with leukocytes, through a device for clearing from interferon; combining the plasma, or plasma with leukocytes, after clearance from interferon, with the previously removed blood cells; and returning the combined blood to the patient.

In another modification, the device 60 utilizes a combined sorbent having a first component for absorbing interferon from the blood, plasma or plasma with leukocytes, and a second component that selectively absorbs T-lymphocytes from the blood, plasma or plasma with leukocytes.

In still another modification, the device 60 utilizes a combined sorbent absorbing transplantation antigens. Yet another embodiment utilizes a combined sorbent having a first component for absorbing interferon, a second sorbent absorbing transplantation antigens, a third sorbent for absorbing T-lymphocytes, and a fourth sorbent for absorbing antibodies to transplantation antigens. In addition, the device utilizes means (antibodies, enzymes, etc.) for clearance of blood from biological agents participating in immune response and transplant rejection.

By utilizing a combined sorbent, the effectiveness of the invention is enhanced.

Suitable sorbents for interferon used with the present invention include anti-interferon globulins against different types of interferon, obtained from animals or by monoclonal antibodies techniques; albumen; and BLUE DEXTRAN 2000 (as described in U.S. Pat. No. 4,172,071).

Thus, in accordance with this invention the clearing of interferon from the organism after transplantation produces immunosuppression, which in turn leads to the suppression of the rejection process.

I claim:

1. In a method of developing immunosuppression in a patient after the transplantation of foreign cells, tissues and organs, using an apparatus having, in continuous fluid communication, an inlet tube, absorbing means for absorbing and thereby removing interferon from the whole blood, and an outlet tube, said method comprising:
   connecting the inlet tube of said apparatus to a blood vessel of a patient and connecting the outlet tube of said apparatus to a vein of the patient;
   removing blood from the blood vessel of the patient;
   passing the removed blood through the absorbing means for absorbing interferon to thereby reduce the amount of interferon in the blood; and
   returning the blood to the vein of the patient,
   the improvement comprising:
   said absorbing means comprising a combined sorbent clearing agent having a first sorbent for absorbing interferon and a second sorbent absorbing T-lymphocytes.

2. In a method of developing immunosuppression in a patient after the transplantation of foreign cells, tissues and organs using an apparatus having, in continuous fluid communication, an inlet tube, absorbing means for absorbing and thereby removing interferon from the whole blood, and an outlet tube, said method comprising:
   connecting the inlet tube of said apparatus to a blood vessel of a patient and connecting the outlet tube of said apparatus to a vein of the patient;
   removing blood from the blood vessel of the patient;
   passing the removed blood through the absorbing means for absorbing interferon to thereby reduce the amount of interferon in the blood; and
   returning the blood to the vein of the patient,
   the improvement comprising;
   said absorbing means comprising a combined sorbent clearing agent having a first sorbent for absorbing interferon, a second sorbent absorbing transplantation antigens, a third sorbent for absorbing T-lymphocytes and a fourth sorbent for absorbing antibodies to transplantation antigens.

3. In a method of developing immunosuppression in a patient after the transplantation of foreign cells, tissues and organs utilizing an apparatus having, in fluid communication with each other, an inlet tube, means for separating plasma from whole blood, absorbing means for absorbing and thereby removing interferon from the plasma, and an outlet tube, said method comprising:
   connecting the inlet tube of the apparatus to a blood vessel of a patient and connecting the outlet tube to a vein of the patient;
   removing blood from the blood vessel of the patient;
   separating the removed blood into blood cells and plasma;
   passing the plasma through absorbing means for absorbing interferon from the plasma to thereby reduce the level of interferon within the plasma;
   combining the plasma having a reduced level of interferon with the blood cells previously removed from the blood; and
   returning the combined blood cells and plasma to the vein of the patient,
   the improvement comprising:
   said absorbing means comprising a combined sorbent clearing agent having a first sorbent for absorbing interferon and a second sorbent absorbing T-lymphocytes.

4. In a method of developing immunosuppression in a patient after the transplantation of foreign cells, tissues and organs utilizing an apparatus having, in fluid communication with each other, an inlet tube, means for separating plasma from whole blood, absorbing means for absorbing and thereby removing interferon from the plasma, and an outlet tube, said method comprising:
   connecting the inlet tube of the apparatus to a blood vessel of a patient and connecting the outlet tube to a vein of the patient;
   removing blood from the blood vessel of the patient;

separating the removed blood into blood cells and plasma;

passing the plasma through absorbing means for absorbing interferon from the plasma to thereby reduce the level of interferon within the plasma;

combining the plasma having a reduced level of interferon with the blood cells previously removed from the blood; and returning the combined blood cells and plasma to the vein of the patient, the improvement comprising:

said absorbing means comprising a combined sorbent clearing agent having a first sorbent for absorbing interferon, a second sorbent absorbing transplantation antigens, a third sorbent for absorbing T-lymphocytes, and a fourth sorbent for absorbing antibodies to transplantation antigens.

* * * * *